(12) United States Patent
Swamy et al.

(10) Patent No.: US 9,750,463 B2
(45) Date of Patent: Sep. 5, 2017

(54) RESPIRATORY STRESS DETECTION

(71) Applicant: General Electric Company, Schenectady, NY (US)

(72) Inventors: Gokul Swamy, Bangalore (IN); Sahika Genc, Niskayuna, NY (US); Hariharan Ravishankar, Bangalore (IN); Aditya Saha, Bangalore (IN)

(73) Assignee: General Electric Company, Niskayuna, NY (US)

( * ) Notice: Subject to any disclaimer, the term of this patent is extended or adjusted under 35 U.S.C. 154(b) by 508 days.

(21) Appl. No.: 14/101,663

(22) Filed: Dec. 10, 2013

(65) Prior Publication Data

US 2015/0157275 A1 Jun. 11, 2015

(51) Int. Cl.
*A61B 5/00* (2006.01)
*A61B 5/08* (2006.01)
(Continued)

(52) U.S. Cl.
CPC .......... *A61B 5/7275* (2013.01); *A61B 5/0816* (2013.01); *A61B 5/7203* (2013.01); *A61B 5/002* (2013.01); *A61B 5/0022* (2013.01); *A61B 5/01* (2013.01); *A61B 5/021* (2013.01); *A61B 5/024* (2013.01); *A61B 5/02055* (2013.01); *A61B 5/0836* (2013.01); *A61B 5/14532* (2013.01); *A61B 5/14542* (2013.01); *A61B 5/201* (2013.01); *A61B 5/202* (2013.01); *A61B 5/7246* (2013.01); *A61B 5/7264* (2013.01); *A61B 5/746* (2013.01)

(58) Field of Classification Search
CPC combination set(s) only.
See application file for complete search history.

(56) References Cited

U.S. PATENT DOCUMENTS

| 4,422,458 A | 12/1983 | Kravath |
| 8,028,701 B2 | 10/2011 | Al-Ali et al. |

(Continued)

OTHER PUBLICATIONS

Charbonnier, Sylvie. "On line extraction of temporal episodes from ICU high-frequency data: a visual support for signal interpretation." Computer methods and programs in biomedicine 78.2 (2005): 115-132. (Charbonnier).*

(Continued)

*Primary Examiner* — Michael Kahelin
*Assistant Examiner* — Mitchell E Alter
(74) *Attorney, Agent, or Firm* — Pabitra K. Chakrabarti

(57) ABSTRACT

Embodiments of the disclosure are directed to a system for analysis of respiratory distress in hospitalized patients. The system performs multi-parametric simultaneous analysis of respiration rate (RR) and pulse oximetry ($SpO_2$) data trends in order to gauge patterns of patient instability pertaining to respiratory distress. Three patterns in $SpO_2$ and RR are used along with LOWESS algorithm and Chauvenets criteria for outlier rejection to obtain robust short term and long term trends in RR and $SpO_2$. Pattern analysis detects the presence of any one of three pattern types proposed. Further, a learning paradigm is introduced to find unknown instances of respiratory distress. This algorithm in conjunction with the learning model allows early detection of respiratory distress in hospital ward and ICU patients.

21 Claims, 9 Drawing Sheets

(51) Int. Cl.
A61B 5/0205 (2006.01)
A61B 5/145 (2006.01)
A61B 5/20 (2006.01)
A61B 5/083 (2006.01)
A61B 5/021 (2006.01)
A61B 5/024 (2006.01)
A61B 5/01 (2006.01)

(56) References Cited

U.S. PATENT DOCUMENTS

| | | |
|---|---|---|
| 8,437,824 B2 | 5/2013 | Moon et al. |
| 8,475,388 B2 | 7/2013 | Ni et al. |
| 8,498,683 B2 | 7/2013 | Price et al. |
| 2010/0113909 A1* | 5/2010 | Batchelder ......... A61B 5/14551 600/364 |
| 2011/0029248 A1 | 2/2011 | Saeed et al. |
| 2011/0066062 A1 | 3/2011 | Banet et al. |

OTHER PUBLICATIONS

Charbonnier, Sylvie, and Francois Portet. "A self-tuning adaptive trend extraction method for process monitoring and diagnosis." Journal of Process Control 22.6 (2012): 1127-1138 (Charbonnier 2012).*

Charbonnier, Sylvie, and Sylviane Gentil. "On-line adaptive trend extraction of multiple physiological signals for alarm filtering in intensive care units." International Journal of Adaptive Control and Signal Processing 24.5 (2010): 382-408 (Charbonnier 2010).*

Cretikos et al., "Respiratory rate: the neglected vital sign", The Medical Journal of Australia, vol. 188, Issue 11, pp. 657-659, 2008.

Lynn et al., "Patterns of unexpected in-hospital deaths: a root cause analysis.", Patient Safety in Surgery, vol. 5, pp. 1-24, Feb. 11, 2011.

Addison et al., "Developing an algorithm for pulse oximetry derived respiratory rate (RRoxi): a healthy volunteer study", Springer Link, vol. 26, Issue 1, pp. 45-51, Feb. 2012.

* cited by examiner

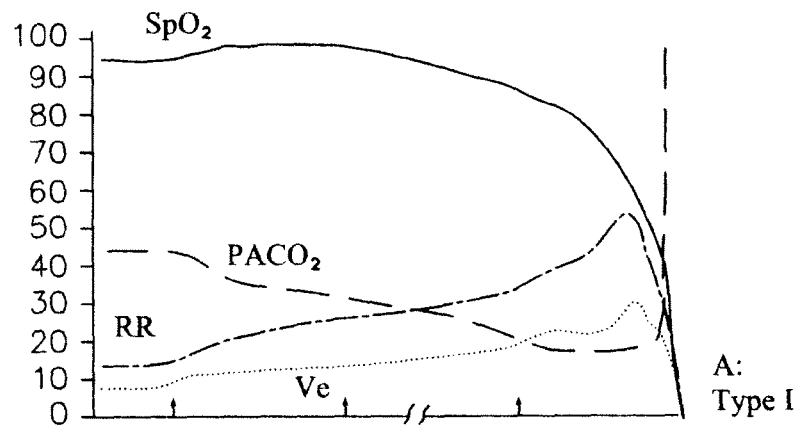
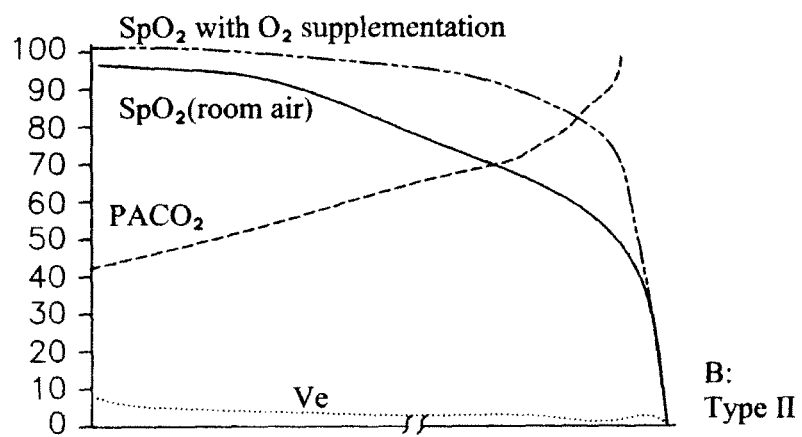
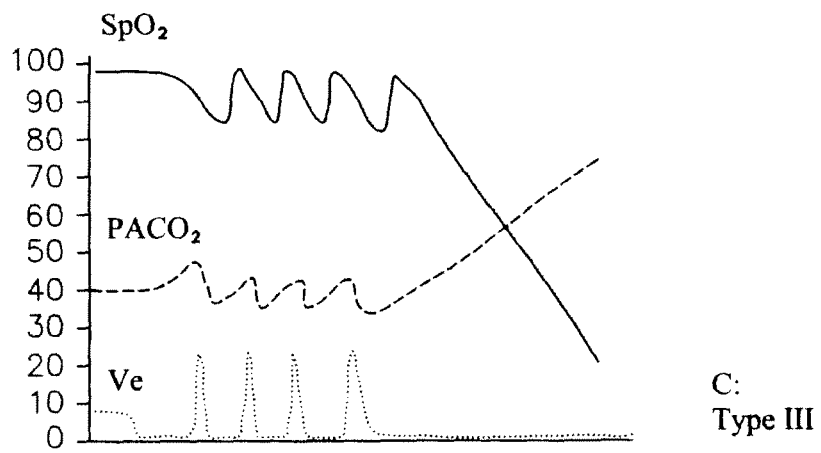
Fig. 1 (Prior Art)

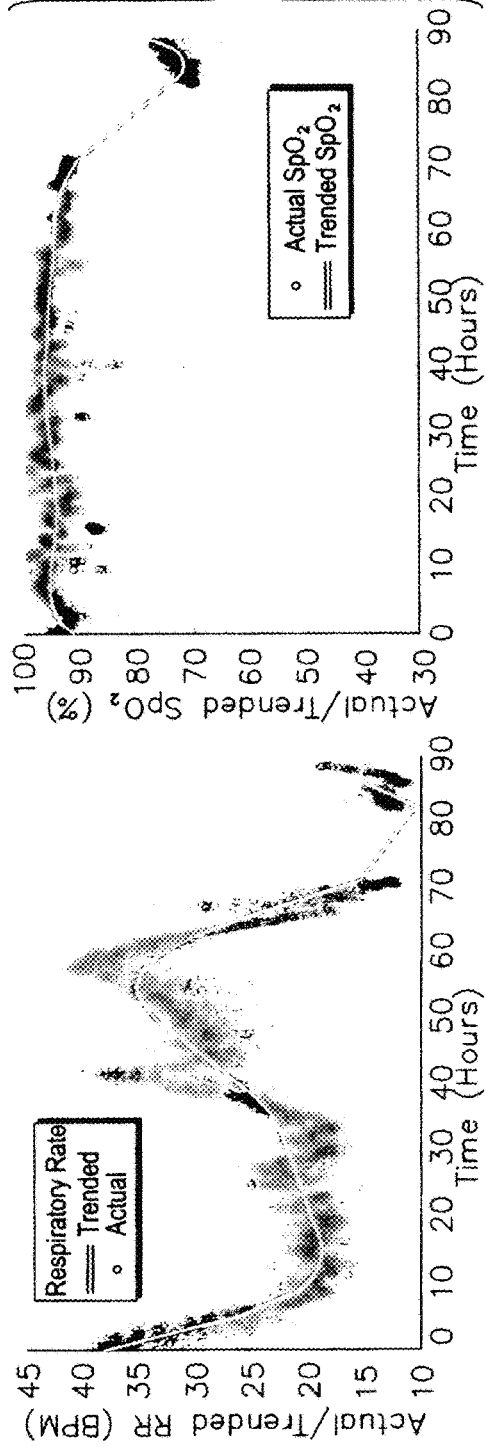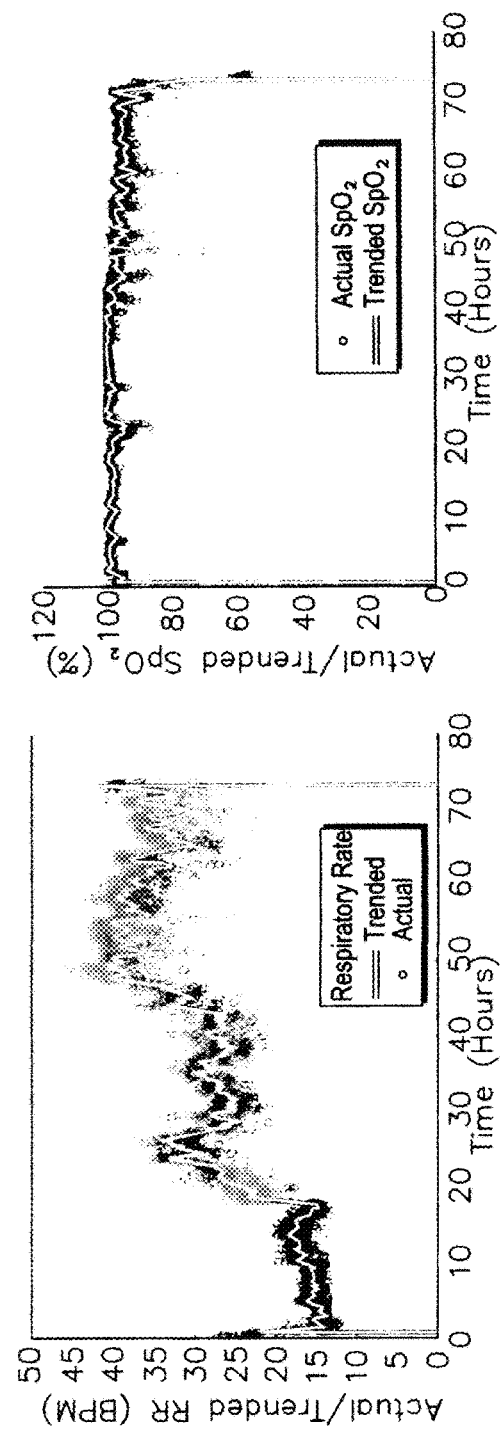

RESPIRATORY STRESS DETECTION

FIELD

Embodiments relate generally to analysis of respiratory distress, and more particularly, to detection of respiratory distress in hospitalized patients.

BACKGROUND

Respiratory rate (RR) as referred to as breathing rate, is an indicator of patient health with particular relevance to respiratory and cardiovascular functions. Respiratory rate exceeding 27 breaths per minute has been found to be the most important predictor of cardiac arrests in hospital wards. In another study it was found that more than 50% of the patients suffering an adverse event in a hospital had a respiratory rate greater than 24 breaths per minute up to 24 hours before the event. In spite of this, respiration rate is often a neglected vital sign not routinely measured in clinical practice. One reason for this is that the manual measurement of respiration rate (counting breaths at the patient bedside) is a cumbersome process. Furthermore, measurement of respiration rate does not yield continuous estimates of respiration rate and has a high likelihood of missing important respiration events during the unmonitored period. In addition, methods for unobtrusive continuous respiration rate estimation using, for example, impedance Plethysmography (IP), have poor measurement accuracy owed largely to algorithmic insufficiency.

In the absence of a reliable respiration rate measure, a patient's peripheral oxygen saturation ($SpO_2$) estimates are utilized as a parameter to detect stress, as indicated when $SpO_2$ values drop below a preset threshold (usually 85-90%). The $SpO_2$ estimates, however, are a very late indicator of patient distress since any lack of oxygenation is often compensated by an increased ventilation drive. When the $SpO_2$ reading drops below the preset threshold, patient status is already severely deteriorated. Therefore, $SpO_2$ alone is not sufficient to detect patient distress.

Rather, trends in respiration rate and $SpO_2$ offer insight into patient status such as the indicated three patterns of patient distress (patterns in $SpO_2$ and RR), noted as the most likely to be encountered in a hospital environment. Three characteristic multi-parametric trend patterns named as Type I, II and III (FIG. 1, PRIOR ART) are explained as:

Type I (FIG. 1A): Hyperventilation Compensated Respiratory Distress (e.g. Sepsis, PE, CHF)—A patient has a gradual decrease in $SpO_2$ with compensatory hyperventilation.

Type II (FIG. 1B): Progressive unidirectional hypoventilation—A patient has a progressive fall in minute ventilation ($V_e$: Volume inhaled or exhaled from a person's lungs per minute) and $SpO_2$ most often brought about my narcotic (sedative) overdose.

Type III (FIG. 1C): Sentinel rapid airflow/$SpO_2$ reductions followed by precipitous $SpO_2$ fall—This type of pattern is most often noted in patients with sleep apnea wherein breathing is characterized by alternating patterns of hyperventilation and no breath. Death in most instances is a result of arousal failure after a prolonged apnea.

As shown in FIG. 1, $SpO_2$ is a late indicator of an adverse event. By the time $SpO_2$ starts to rapidly decline, the patient is in distress: The $PACO_2$ has been declining and RR and $V_e$ have been increasing. Hospitals fail to recognize the patterns as referenced, as well as lack the systems to identify or characterize these patterns. Current hospital monitoring also fails to identify these trends during vital sign collection and fails to offer detection systems or processing that have the capability to analyze data and deliver an output to realize early patient distress. A multitude of false alarms further inhibits care at the patient's bedside in most urgent situations, increasing the risk for a critical care patient and inhibiting prioritized response of one patient's critical state as compared to another. When an alarm goes off, a silence action is implemented by a clinician or after a time delay. The increase in alarm systems at the bedside has led to increased silencing as the alarms have become monotonous and overused. Thus, this leads to mistakenly silencing critical events.

The invention disclosed in the following addresses the issues as indicated above and further resolves the need for clinical systems that currently lack the monitoring and analytical capabilities that would prevent false alarm fatigue and alert providers earlier as to deteriorating patient condition.

SUMMARY

Embodiments of the invention employ a regression algorithm coupled with an outlier rejection scheme to accurately estimate trends in RR and $SpO_2$ waveforms; these trends are then utilized in detecting multi-parametric patterns of progressing patient instability.

In one embodiment, a computer-implemented method of detecting respiratory distress in a patient is disclosed, the computer including a processor, the method comprising acts of (a) monitoring patient data over a time period, the patient data comprising measures of respiratory rate and $SpO_2$ recorded simultaneously in a storage component; (b) tracking the measures of respiratory rate and $SpO_2$ over the time period, individually, in corresponding least squares regression models; (c) analyzing the least squares regression models of each of the measures of respiratory rate and $SpO_2$ to remove noisy deviation from respective measures of respiratory rate and $SpO_2$; and (d) identifying multiple segmented trends in each of the least squares regression models as one of an uptrend, downtrend, or neutral, wherein each of the trends in sequential combination establish a pattern; and wherein the pattern triggers an alarm as an early warning system of patient distress and prevents false alarm fatigue. In one aspect, the computer-implemented method further comprises a step of correlating the measures of respiratory rate and $SpO_2$, and the correlation is recognized in real-time as a pattern. One embodiment of the computer-implemented method allows a pattern to be identified as one of three types that include: (a) Type I: gradual decrease in $SpO_2$ with compensatory hyperventilation; (b) Type II: progressive decreases in minute ventilation and $SpO_2$; or (c) Type III: Guarded rapid airflow including $SpO_2$ reductions followed by precipitous $SpO_2$ fall. Another embodiment allows the pattern to be learned, such that it may be unique to a patient or not previously recognized.

Another aspect of the invention provides an early warning system of patient distress, and indicates early detection of at least one life event including, but not limited to one of cardiopulmonary arrest, respiratory failure, renal failure, sepsis, and/or re-intubation risk. The computer-implemented method utilizes patient data that includes measures of a plurality of vital signs, in combination such that the tracking step collects and records this data.

In one embodiment of the computer-implemented method the measures of respiratory rate and $SpO_2$, individually, do not trigger an alarm; and, changes in the measures of respiratory rate and SpO$_2$, in combination, trigger an alarm. In one aspect, the trending classification of respiration rate and SpO$_2$, in combination, may be a learned pattern and therefore may trigger or designate an alarm or alarm sequence. Any changes in the trending classification, or recognition of a second learned pattern, re-evaluates the sequence of events and becomes part of the triggered alarm sequence.

Embodiments of the invention identify multiple segmented trends that are estimated amongst a variety of data points, while data is screened for noisy variation and anomalies through statistical verification such that patterns of progressing patient instability can be detected.

Embodiments of the invention include the computerized system for early detection of respiratory distress comprising: one or more sensors attached to a patient to monitor a plurality of vital signs; a monitoring system connected to the one or more sensors; a storage component connected to the monitoring system to record patient data, wherein patient data comprises measures of the plurality of vital signs including respiratory rate and SpO$_2$ of the patient; a processor interconnected with the monitoring system and the storage component to analyze the patient data over a time period such that segmented trends are identified in the measures of respiratory rate and SpO$_2$ and define one or more patterns to characterize patient status. The segmented trends are identified as one of an uptrend, downtrend, or neutral using a least squares regression model. The segmented trends in sequential combination establish the pattern in real-time. Furthermore, in one aspect, the pattern triggers an alarm to provide an early warning system of patient distress. In another aspect, the pattern triggers a critical alarm and prevents false alarm fatigue.

In one embodiment, the computerized system records and correlates measures of respiratory rate and SpO$_2$ simultaneously. Aspects of the invention incorporate a plurality of vital signs including any one or more of body temperature, pulse or heart rate, blood pressure, blood glucose, urine production, urinary incontinence, and end-tidal CO$_2$, among others. The vital signs can, in turn, be correlated with the respiratory rate and SpO$_2$, alone or in combination, to characterize one or more patterns that alert a clinician as to patient distress. In one aspect, patient history data is integrated with the storage component to characterize one or more patterns. Embodiments of the system incorporate processes for learning patterns, while integrating various data, including, but not limited to, patient use of medications, sedatives, analgesics, vitamins, and supplements.

In various embodiments, the ongoing monitoring and recording of patient data allows for continuous system analytics that can recognize and learn patterns to better inform and alert clinicians in a healthcare setting. Use of the system outside of healthcare, may be employed in mining, hiking to high altitudes, and other activities that may potentially cause respiratory distress. Such uses may be modified and configured depending upon geospatial location, atmospheric conditions, weather, and patient stability, among other factors.

BRIEF DESCRIPTION OF THE DRAWINGS

Features and aspects of embodiments are described below with reference to the accompanying drawings, in which elements are not necessarily depicted to scale.

FIG. 1 (PRIOR ART) depicts graphical interpretations of respiratory distress preceding unexplained hospital deaths.

FIG. 2 depicts examples of trend estimates using the proposed algorithm, in accordance with one embodiment: FIG. 2A illustrates data trends for a first patient; FIG. 2B illustrates data trends for a second patient.

FIG. 5 illustrates a learning methodology for trend segmentation, in accordance with embodiments of the invention.

DETAILED DESCRIPTION

Figure 3:
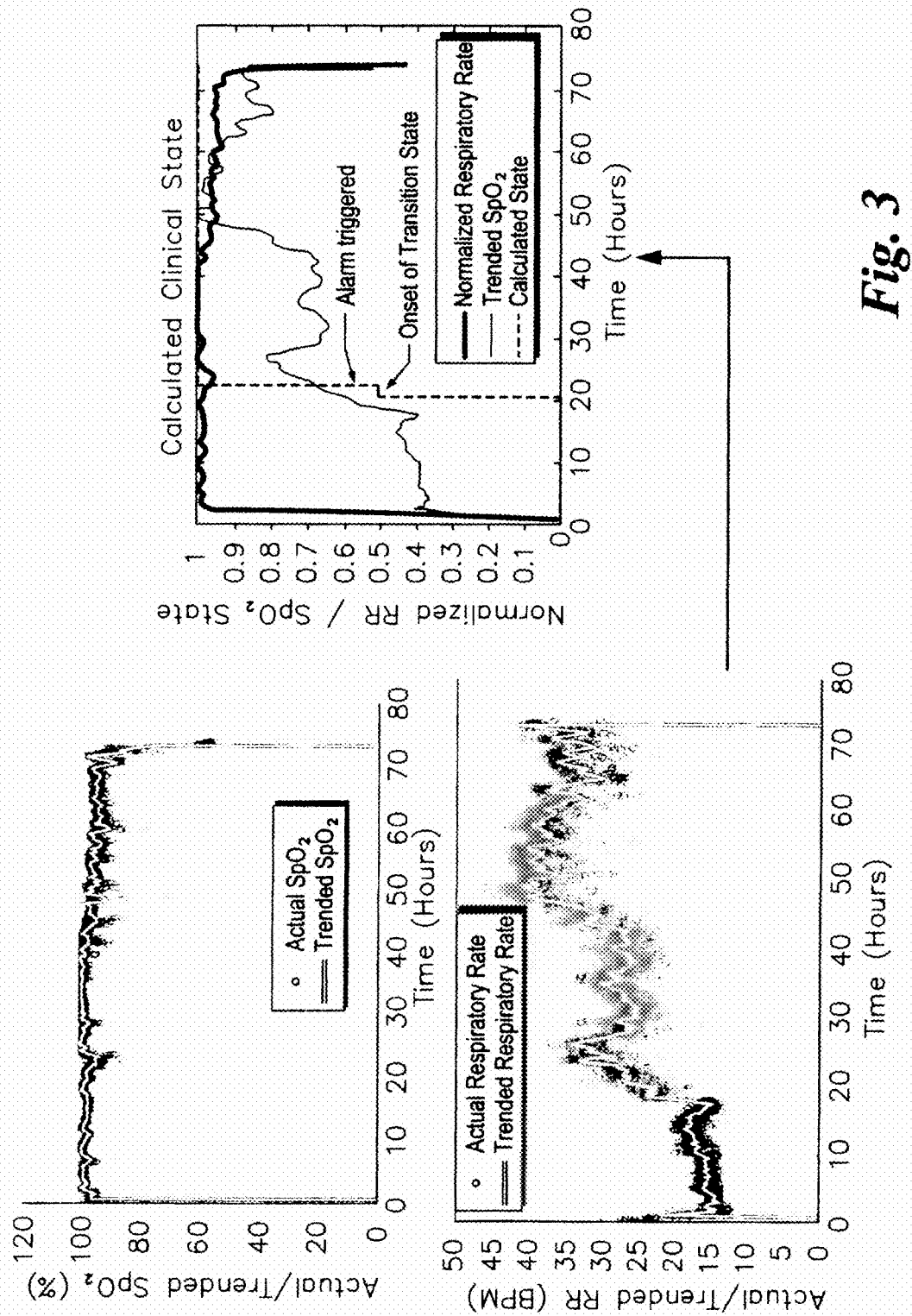
FIG. 3 depicts an aspect of the invention in one embodiment utilizing the Type-1 pattern recognition that triggers a transition state: SpO$_2$ and RR trends are identified to calculate a patient's critical state.

Embodiments are directed to systems and methods of utilizing detection methodologies to identify anomalous observations as based on statistical patterns in collected data to recognize patient distress and trigger an alarm at an early stage of distress.

In this invention, an algorithm is described to be utilized with systems to detect respiratory rate and SpO$_2$ so that the system quickly identifies the three types of trend patterns based on an analysis of the respiration rate and SpO$_2$ time series. In addition, the algorithm is extended to recognize and detect other instances of respiratory distress by learning prior patterns of patient instability.

Method

For exemplary purposes, and not limitation, two different methods to tackle the problem of early detection of respiratory distress are characterized. In the first method, a trending algorithm captures the trends in the SpO$_2$ and RR waveforms. Based on the trend estimates, a scheme is utilized to identify trend patterns which are likely to be an early indicator of patient distress. Each trend pattern identified closely mirrors a pattern as one of:

Type I: Hyperventilation Compensated Respiratory Distress (e.g. Sepsis, PE, CHF)—gradual decrease in SpO$_2$ with compensatory hyperventilation.

Type II: Progressive unidirectional hypoventilation—progressive fall in minute ventilation and SpO$_2$, most often brought about my narcotic (sedative) overdose.

Type III: Sentinel rapid airflow/SpO$_2$ reductions followed by precipitous SpO$_2$ fall—This type of pattern is most often noted in patients with sleep apnea wherein breathing is characterized by alternating patterns of hyperventilation and no breath. Death in most instances is a result of arousal failure after a prolonged apnea.

In another approach, a learning algorithm automatically identifies uptrends, downtrends and flat-trends (neutral, or no change) in the $SpO_2$ and RR time series. This information then is integrated into a model to predict the onset of respiratory distress. Further detail of the systems and methods are described in detail in the following subsections.

Model Based Pattern Recognition

In order to accurately estimate the trends in the $SpO_2$ and RR waveforms, a locally weighted least squares fitting algorithm is used which incorporates an outlier rejection step using criteria as stated in the algorithm that follows:

Given a point $x_i$ and its neighborhood estimate (as associated with x variables within a certain time period), an m-order least squares fit by minimizing the following penalty function is utilized:

$$C(\beta_0, \ldots, \beta_n, \lambda) = \sum_{k=1,n} w_k (y_k - \beta_0 - \beta_1 x_k \ldots - \beta_m x_k^m) + \lambda \sum_{k=2,n} |y_k - y_{k-1}|^2$$

where $y_k$ is the current estimate of the parameter and the time instance $x_k$. As compared to the traditional least squares fit, the LOESS method includes an extra penalty term that results in a normalized solution. The choice of the parameter lamda ($\lambda$) and the degree of the polynomial m are instrumental in deciding the smoothness of the generated fit. The variables $w_k$ represent a weighting function and could be appropriately chosen to minimize the influence of outliers.

Examples of trend estimates using the proposed algorithm are shown in FIG. 2. As illustrated, the left graph in FIG. 2A designates RR rate data points (o) for a patient over a time period of 90 hours, with corresponding trends in $SpO_2$ on the right. In FIG. 2B, the generated trend in RR (indicated by the solid line) for another patient corresponds with the simultaneous recording of $SpO_2$ data points and trends estimated in the graph on the bottom right.

Based on the generated trends, an embodiment of the system identifies each of the three types of patterns (Type I, II, and III) of respiratory distress. An example of Type-1 pattern detection is illustrated in FIG. 3. The Type-I pattern uses an algorithm that looks for a rise in RR rate with a concurrent fall in $SpO_2$. As shown in FIG. 3, as the RR rate rises and $SpO_2$ begins to fall, a transition state is triggered (around about 20 hours). On continuation of this pattern for a preset time, an alarm is triggered around about 23 hours indicating developing patient distress. It is recognized that both the RR rate and $SpO_2$ may not have risen or fallen enough, respectively, to trigger their individual alarms. Thus, the method identifies the interplay between these physiological parameters and gives an early indication of patient distress. Since the trend generation algorithm is agnostic to outliers, noisy deviations of RR and $SpO_2$ estimates are overlooked and therefore largely overcomes the problem of alarm fatigue due to noisy measurements.

In another embodiment, Type II pattern detection follows a similar logic such that the algorithm searches for a gradual downtrend in RR with a concurrent fall in $SpO_2$. As compared to Type I and Type II patterns, the Type III pattern of respiratory distress follows a cyclical pattern of apnea, hyperventilation, apnea, hyperventilation . . . and so on. An advanced signal processing algorithm is developed to detect these respiratory arrhythmias.

Embodiments of the invention employ the regression algorithm as described coupled with an outlier rejection scheme to accurately estimate trends in RR and $SpO_2$ waveforms. The trends in the waveforms are then utilized in detecting multi-parametric patterns of progressing patient instability.

Trend Classification and State Space Method

In the previous embodiment, a method for early detection of respiratory distress utilized trend analysis of RR and SpO2 waveforms. In one aspect, the method is based on a modeling principle involving detection of prior patterns in these trends. In another embodiment, the approach is utilized to detect respiratory distress in cases where these prior patterns (Types I, II, and III) may not manifest. The embodiment learns variable patterns of respiratory distress based on previous learning examples.

Prior to learning patterns of respiratory distress, the trend is decomposed into its constituent components for further analysis. Trend components primarily comprise an 'uptrend', 'downtrend' and 'neutral'. Further classification is also possible based on classifying the uptrend or downtrend into mild or severe categories. Subsequent to decomposing the trend into its constituent components, the system proceeds to utilize the information in a Hidden Markov Model (HMM) framework for early prediction of respiratory distress. In the HMM framework, the state is not directly visible; but output, dependent on the state, is visible. Each state has a probability of distribution over the possible outputs (i.e. The process itself cannot be observed, and only the sequence of events or measurements can be observed and recorded). Therefore the sequence of outputs generated by the HMM gives some information about the sequence of states. The steps are explained as follows:

A. Trend Classification

Figures 4, 4A, 4B:
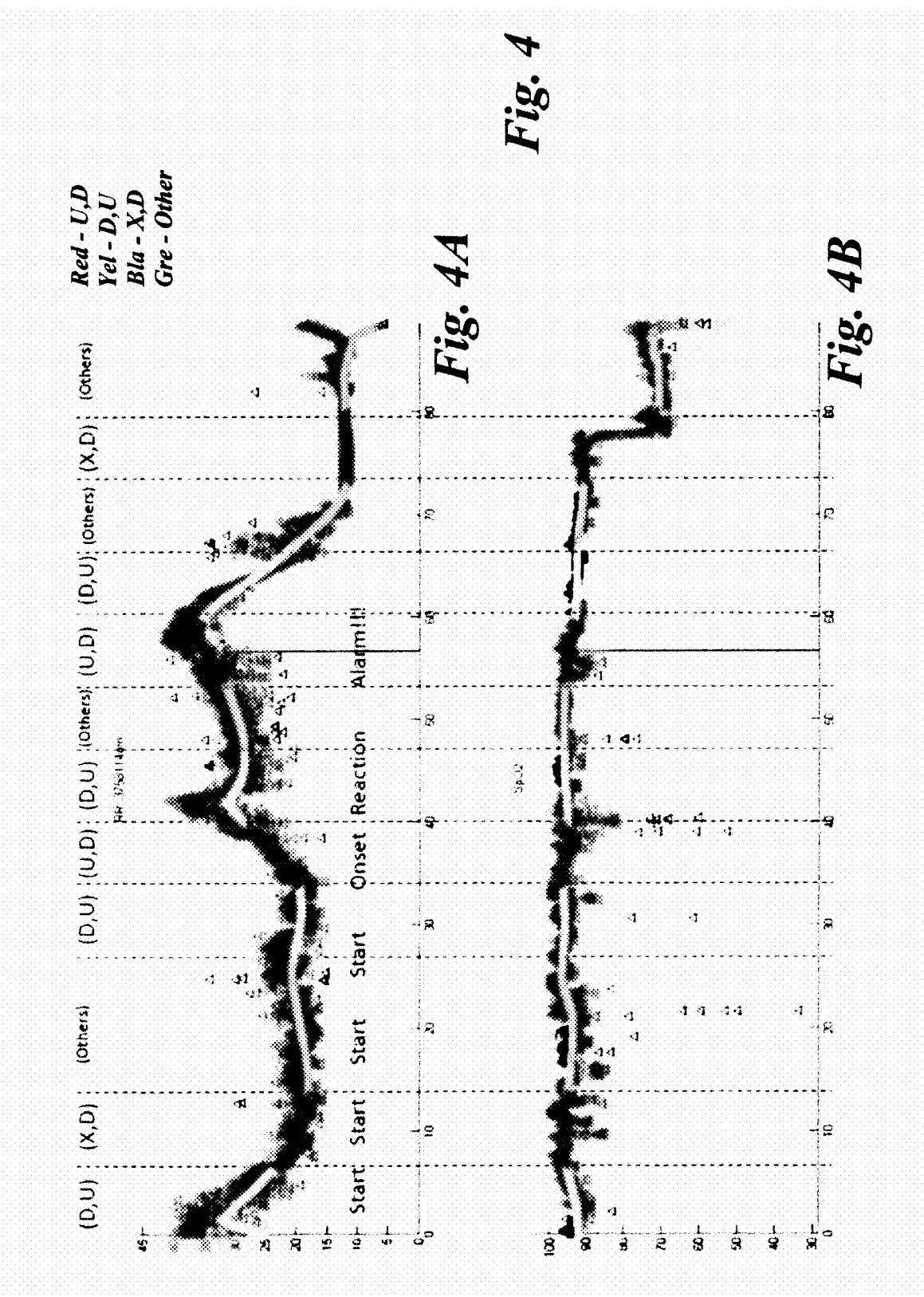
FIG. 4 depicts the classification of the trend into its constituent components, in accordance with one embodiment.
FIG. 4A illustrates RR data for a patient with the patient's corresponding SpO$_2$ data in FIG. 4B.

Given a trend, the goal is to classify the portions of the trend into one of three categories 'uptrend', 'downtrend' and 'neutral', constituent components of the overall trending in accordance with one embodiment. An exemplary classification is illustrated in FIG. 4 where each segmented portion of the trend denotes an uptrend, a downtrend, a neutral, or alarm. These classifications in the algorithm allow for trend segmentation and analyzing the segmented trends within the linear approximation algorithm.

As depicted in FIGS. 4A and 4B, the identified patterns are identified by segmented lines, but typically designated in color codes to highlight various local events that are helpful in detecting distress. Here, for example, Type-1 respiratory distress is recognized. The top plot in FIG. 4A is the respiration rate for a patient in breaths per minute over time in hours and the bottom plot in FIG. 4B is the corresponding oxygen saturation for the patient in percentage over time in hours. In one embodiment, for example and not limitation, the color code is as follows:

Red—Simultaneous increase in RR and decrease in $SpO_2$ (principal indicator of Type 1 pattern)

Yellow—Simultaneous decrease in RR and increase in $SpO_2$

Black—Decrease in $SpO_2$ irrespective of the change in RR (when the above two conditions are not met)

Purple—Increase in RR irrespective of the change in $SpO_2$ (when the above conditions are not met)

Green—when none of the above conditions are met—No useful event

Detection of these events using the trend segment classification approach is explained as follows. Each trend segment of FIG. 4B corresponds to each trend that is classified in FIG. 4A and classified as stable (X), up (U), and down (D), and obey the following rules:

Piecewise Linear Approximation: After dividing the trend waveforms into segments, the line segments are fit over the trended RR and $SpO_2$ values observed within the window under consideration. The slope of the line segments is used to classify them into one of the—stable, increase (up) or decrease (down) classes.

Since this classification is purely algorithm driven and not based on manual annotation (See FIG. 8: manual annotation by clinicians), the classification result of the segment may not match suitably with the visual inference. This happens mainly in cases where the change in RR or $SpO_2$ is too small to decipher precisely.

Where the RR or $SpO_2$ values change significantly over the window, the classification may not capture the dynamics properly. This is due to the fact that the classification is based on the properties of the 'line segment' (a line of best-fit); it does not have the capability to capture all higher order variations within the segment As illustrated in FIGS. 4A and 4B, an alarm is triggered when a Type I pattern is recognized. The system 400 is configured to trigger alarms at designated events that are pre-determined patterns or unstable patterns recognized by the algorithm. Specifically, the segmented trends that are better visualized in a color schematic assist the system in identifying patterns early and preventing false alarms. The configuration of the system as mentioned is designed with a micro-analytic focus so that individual segmented trends are identified by the linear approximation as opposed to taking an overall trending visual. Thus, the Drawings disclosed herein have intended to segment the trending line as based on localized data points screening out localized noise and extraneous data in real-time.

Figure 5A:
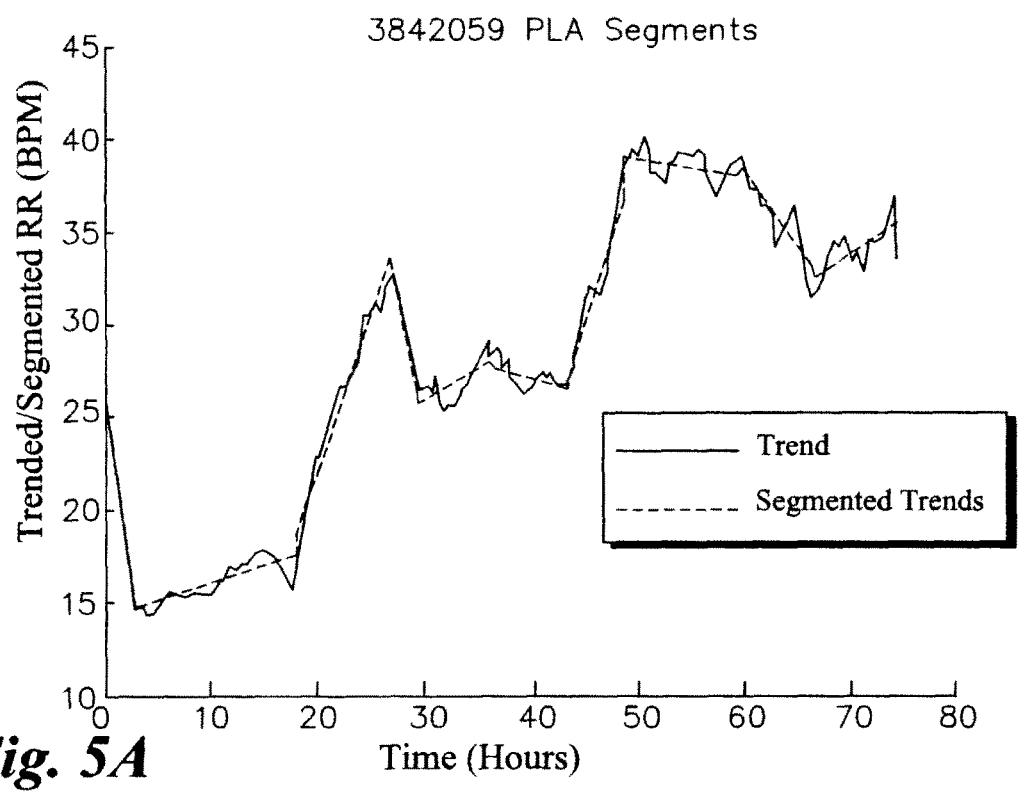
FIG. 5A and FIG. 5B depict trends and segmented trends that are recorded from patient A and patient B, respectively.
Figure 5B:
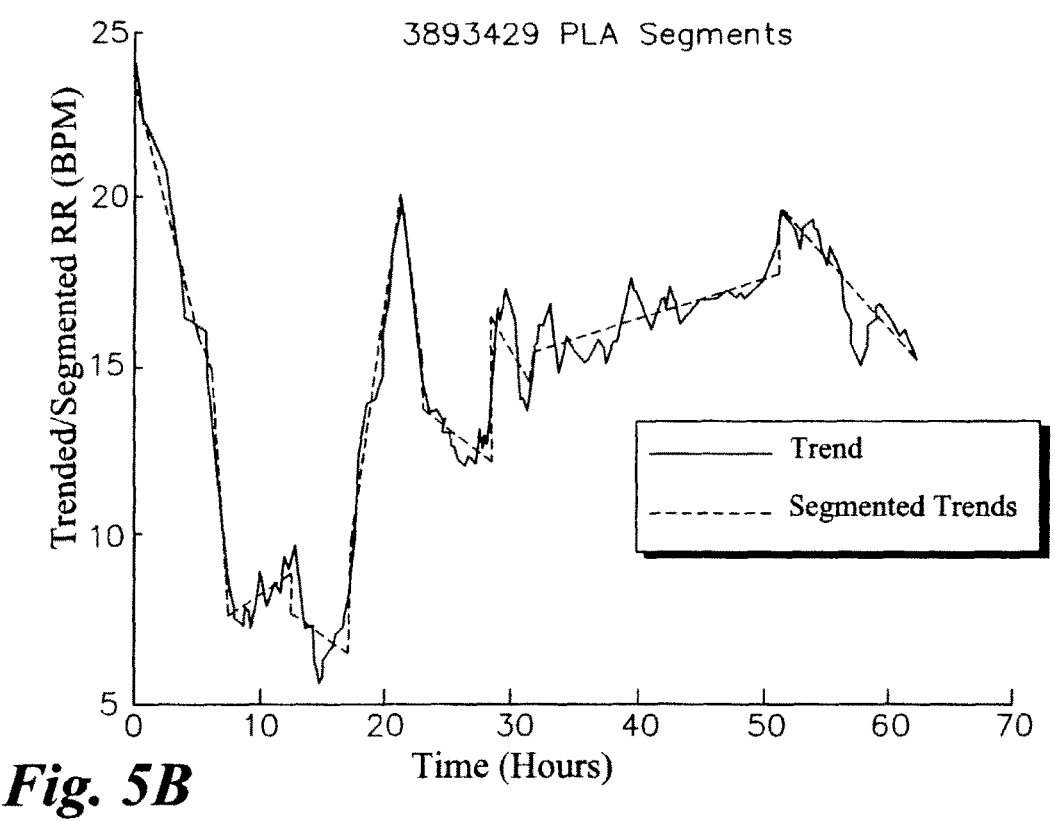

FIG. 5 illustrates a learning methodology for trend segmentation, in accordance with one embodiment. Trends associated with the learning examples in one embodiment are then decomposed into linear segments using the piecewise linear approximation (PLA) algorithm. As depicted, FIGS. 5A and 5B, respectively, each demonstrate trend segmentation as determined by identifying and minimizing outliers while separately characterizing the trend using a linear regression model. FIG. 5A corresponds to data from a first patient; FIG. 5B corresponds to data from a second patient.

Aspects of the method are explained in the following steps:
1) The trends in RR and SpO2 are manually annotated to create a database of learning examples.
2) The trends associated with the learning examples are then decomposed into linear segments using the piecewise linear approximation (PLA) algorithm. Examples of PLA output are shown in FIG. 5. As illustrated, the trend lines are depicted in solid trending segments and the PLA as a dashed line.
3) The linear PLA segments are then input as feature vectors into a decision tree learning algorithm.
4) When a new dataset is encountered (outside of training examples) it is passed through the learned decision tree network to automatically generate the segmented trend.

B. State Space Method

Based on the trend classification in one embodiment, each trend is represented by a 3-tuple time series T: {TY, t, s} where TY denotes uptrend (U), downtrend (D) or neutral (N), t denotes the time duration for which the trend component is active and s denotes the strength (s=0, 1, and 2 for mild, moderate and severe trends respectively) which is representative of the magnitude change in the parameter value over the course of the trend. In one aspect, the trend itself can be characterized by expressing it as $T_{RR/SpO2}=[T_1, T_2, T_3 \ldots T_n]$ where the $T_i$'s are the instances of the trend segments as generated by the decision tree algorithm. An example of such labeling for the trend in FIG. 4 would be $T_{RR/SpO2}=[\{U,2,1\}, \{D,10,2\}, \{N,23,0\}, \{U,16,2\}, \{D,5,1\}, \{U,12,2\}, \{D,13,2\}, \{N,12,0\}]$. In this aspect, $T_{RR/SpO2}$ is referred to as the label vector. The label vector is generated in real-time and is continuously updated as new data comes in. Given the label vector (for both RR and $SpO_2$ trend sequences) as an observation sequence, a state space is defined characterizing an HMM framework for respiratory distress as shown in FIG. 6, also known here as the state space model (SSM) for detecting respiratory distress.

Figure 6:
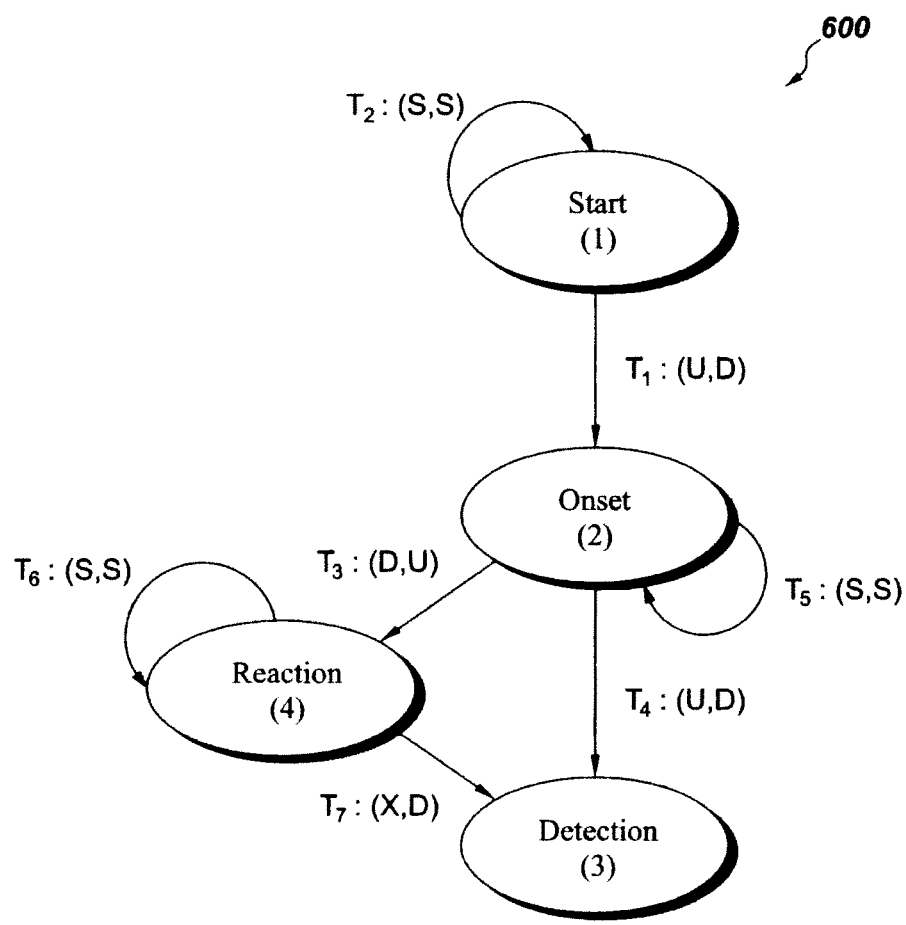
FIG. 6 is a flow diagram in one embodiment as to a state space model for detecting respiratory distress.

In FIG. 6, the flow diagram charts one example of a method of segmenting a digital image, in accordance with one embodiment. A Markov process can be thought of as 'memoryless'; a process satisfies the Markov property if one can make predictions for the future of the process based solely on its present state. In one aspect, one could know the process's full history (i.e., conditional on the present state of the system, its future and past are independent). A Markov process is defined by its set of states, transitions, and events. The Markov process model 600 for Type 1 pattern shown in FIG. 6 comprises four states: (1) "Start", (2) "Onset", (3) "Reaction", and (4) "Detection", which are depicted with circles and state labels inside the circles. Seven transitions include: "$T_1$: Start→Onset", "$T_2$: Start→Start", "$T_3$: Onset→Reaction", "$T_4$: Onset→Detection", "$T_5$: Onset→Onset", "$T_6$: Reaction→Reaction", "$T_7$: Reaction→Detection". Four event labels, "(S, S)", "(U, D)", "(D, U)", "(X, D)", where S, U, and D correspond to stable (S), up (U), and down (D) trends in the time-series signal over a fixed or variable time window, and the first and last letters in the parenthesis separated by a comma correspond to trends in respiration rate and oxygenation, respectively.

The SSM refers to a class of probabilistic graphical models that describe the probabilistic dependence between the latent state variable and the observed measurement. In one aspect, the statistical technique is used to characterize the dynamic features in trending RR and $SpO_2$, also characterized as noisy and temporal.

The parameters of this model are learned using prior training data. Once the model is learned, the most likely state sequence can be predicted using, for instance, the Viterbi back propagation algorithm. The Viterbi algorithm is a dynamic programming algorithm for finding the most likely sequence of hidden states in the context of hidden Markov models. Knowledge of the state sequence enables prediction as to the early onset of respiratory distress.

Results

Prototype versions of an embodiment of the algorithm were tested on a sample dataset of nineteen patients out of which nine patients had respiratory distress while the others did not report any distress. In one aspect, the algorithm accurately determines the onset of respiratory distress in eight out of nine patients with a lead time exceeding 15 hours prior to patient mortality. Thus, the method is able to alert the physician as to a deteriorating patient condition much before the patient undergoes severe health deterioration. In addition, the test on the normal subjects reveals that no alarms are generated for 8 out of 10 patients reflecting a false alarm rate of 20%. Table 1 indicates the early warning capability in one embodiment.

TABLE 1

Early warning capability of an embodiment of the algorithm
as utilized on patients who suffered mortality due to failure

| File Name | Number of hours patient lived | Time when the alarm was triggered (EARLY ALERT) |
|---|---|---|
| 3167864nm | 103.56 | 43.35 |
| 3192258nm | 67.400000 | 30.016667 |
| 3254526nm | 102.550000 | 43.350000 |
| 3340926nm | 26.316667 | 0.000000 |
| 3401319nm | 209.866667 | 30.016667 |
| 3634632nm | 25.800000 | 16.683333 |
| 3758114nm | 88.666667 | 43.350000 |
| 3842059nm | 74.183333 | 43.350000 |
| 3893429nm | 62.266667 | 30.016667 |

Figure 7:
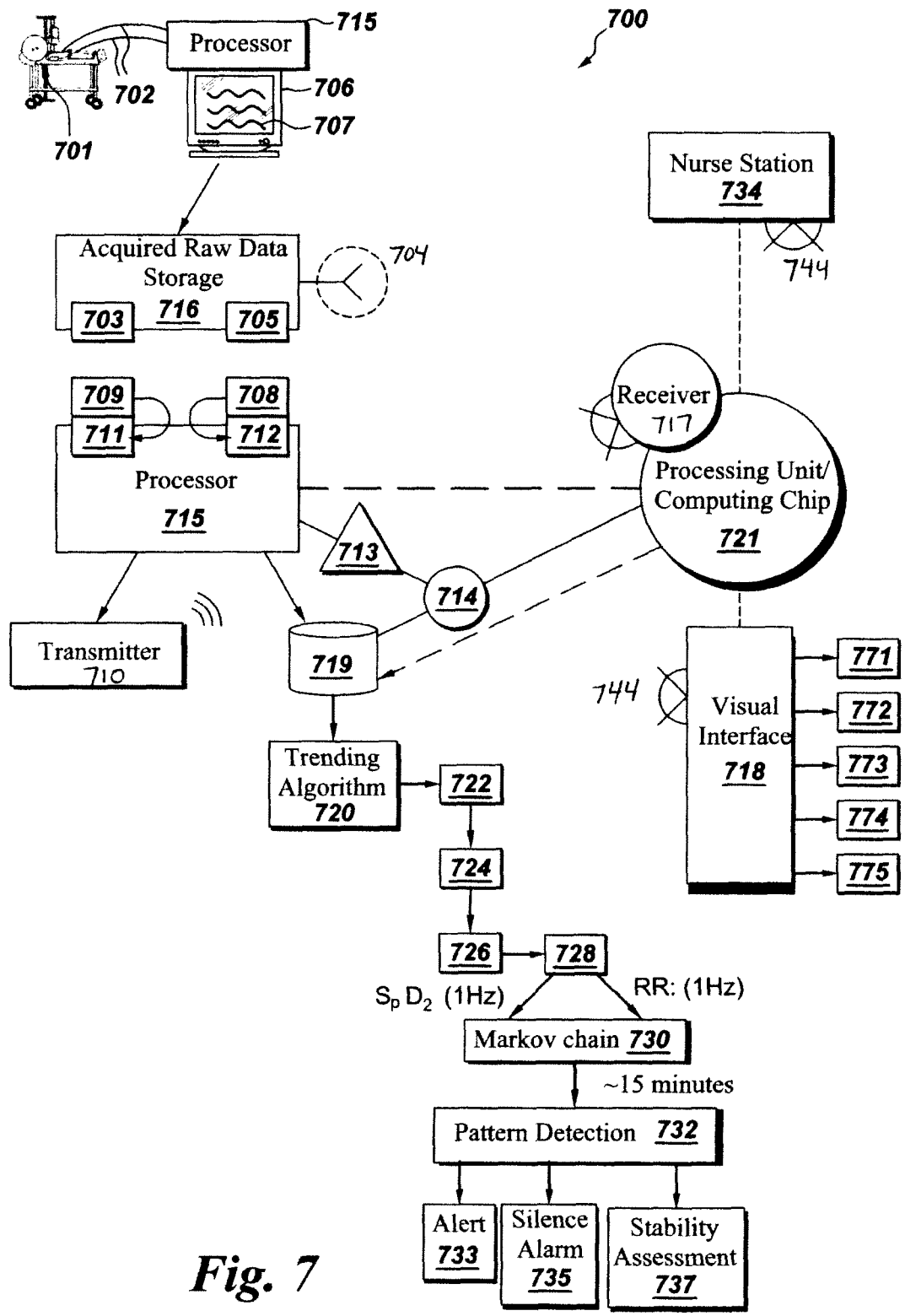
FIG. 7 is a schematic of an example of the system for carrying out one or more embodiments.

As illustrated in FIG. 7, an embodiment of the system 700 is depicted in a schematic. A patient 701 has attached sensors connected by leads 702 to a monitor 706 for monitoring impedance respiration 703 and pulse oximetry 705, the acquired raw data of which is stored in the database 716. Signal quality detection is then optimized: The respiratory rate is extracted by calculating the dominant pulse rate within a specific time frame that includes at least three inhale and exhale periods (e.g., 24 seconds) in the respiration rate form. The dominant pulse rate is calculated from time-frequency representation of the respiration waveform within the specified time frame by determining the frequency components with larger power compared to other frequency components within the admissible respiration rate range (about 5-50 breaths per minute).

From waveform readouts 707 on the monitor 706 from impedance respiration 703, respiratory rate 709 is extracted; from waveform readouts 707 of pulse oximetry 705, oxygen saturation 708 is measured simultaneously. Numerics data from the recording monitors 706 translates respiratory rate 709 as breaths per minute 711. Numerics data from monitors 706 translates oxygen saturation as $SpO_2$ 712 between 0%-100%.

As illustrated, a server 713 is connected to a network 714 within the hospital infrastructure to capture the data for analytics by a processor 715. A database 719 standardizes the information and monitors patient data, on an individualized patient treatment and monitoring protocol.

Aspects of the system 700 allow wireless connectivity 704 of the raw data storage 716 and the database 719 to a network 714 and permit the use of multiple visual interfaces 718, including those such as a television 771, health monitor 772, iPhone 773 or similar device, laptop 774, portable electronics 775, among others. This integration of the system 700 with personal computing devices and portable electronics 775 expands the communication capabilities between clinicians, as well as to facilitate patient observation from remote locations. In one aspect, a processor 715 embedded with Windows® connects to the numeric database processing unit 721 to analyze the data in real-time. In another aspect, the processor 715 is hardwired directly to the database 719.

In one aspect, a transmitter 710 is a separate piece of electronic equipment, or can be an electrical circuit within another electronic device. The receiver 717 as part of the processing unit 721 converts signals into usable information. The receiver 717 and transmitter 710 can also be combined into one unit. The information provided to the transmitter is in the form of an electronic signal, such as an audio (sound) signal from a microphone, a video (TV) signal from a video camera, or in wireless networking 744 a digital signal as from a computer (e.g. devices such as those used as visual or audio interfaces 718 including 771, 772, 773, 774, 775, etc.).

The real-time processor 715 in connection with database 719 has an interface that sees episodic data of lab values, pharmaceutical use, electronic medical records (EMRs), visual and/or clinical notes in combination with the RR and $SpO_2$ data. A trending algorithm 720 is associated with the measurements over a brief period of time between about 2 minutes to about 20 minutes, or even trends realized in less than about a minute. The trends are determined by the sampling rate or as detected over increments of time per individual patient. Characteristics of the signal are defined and any noisy or temporal measures are identified and selected out to more accurately characterize the trend. Averaging data and correlating trends of different parameters can correlate data between parameters as desired. Further averaging and correlating minuscule trends, mini-trends, allows for more specificity and sensitivity in detection and analysis. Irregularity or variance in trending is analyzed during anomaly detection 722. By identifying mini-trends over the course of time, and associating any anomalies, a pattern inquiry 724 identifies a specific pattern. If there is a pattern of interest, pattern classification 726 specifies the type of pattern and is statistically verified in real-time through statistical verification 728. The statistical and temporal properties build and characterize the features that are utilized in pattern recognition; the Markov process model 730 completes the pattern recognition.

In one embodiment, LOWESS line of regression is utilized to mark mini-trends during a time period. Once patterns are recognized, the Markov chain 730 is identified such as "down, down, up" for Type I (as illustrated in FIG. 7). Trending may be characterized by Types I, II, or III, but also learned via ongoing patient monitoring as characteristic and unique to a particular patient. For exemplary purposes, and not limitation, in a timeframe of about 15 minutes, patterns are recognized and type identified at pattern detection 732. The detected pattern is then monitored for sensitivity and specificity to alert a clinician as to patient distress 733, silence false alarms 735, or assess a patient's stability 737, among other conditions as specified in the recognition process. Advantageously, the system and method of recognizing critical alarms sooner as to a patient's respiratory distress can be continuous ongoing real-time monitoring without the manual recording of measurements by a clinician. Further, the arbitrary analysis that is based on a clinician's subjectivity is removed so that critical alarms are quickly identified before a patient is in distress. Also, a clinician realizes the severity of an alarm sooner (and less often) so as to remove any mistaken silencing of alarms and more easily monitor multiple patients in a hospital setting.

Figure 8A:
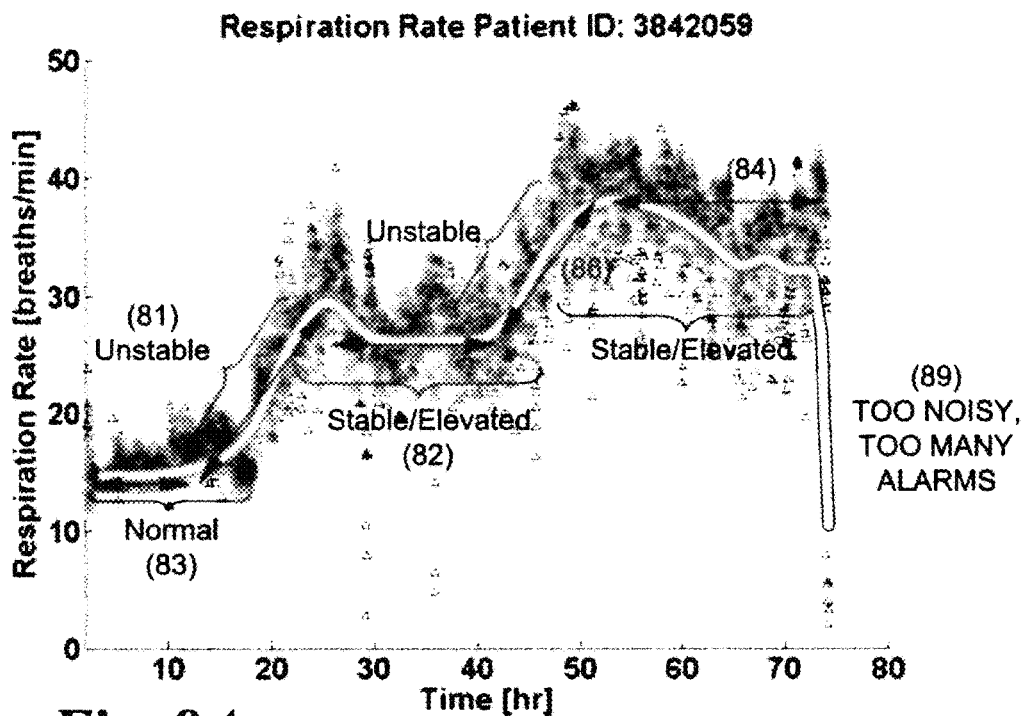
FIG. 8A depicts the use of a system in one embodiment that recognizes patterns in respiratory rate utilizing characterization of trends to address patient stability or instability and prevent overuse of alarms.
Figure 8B:
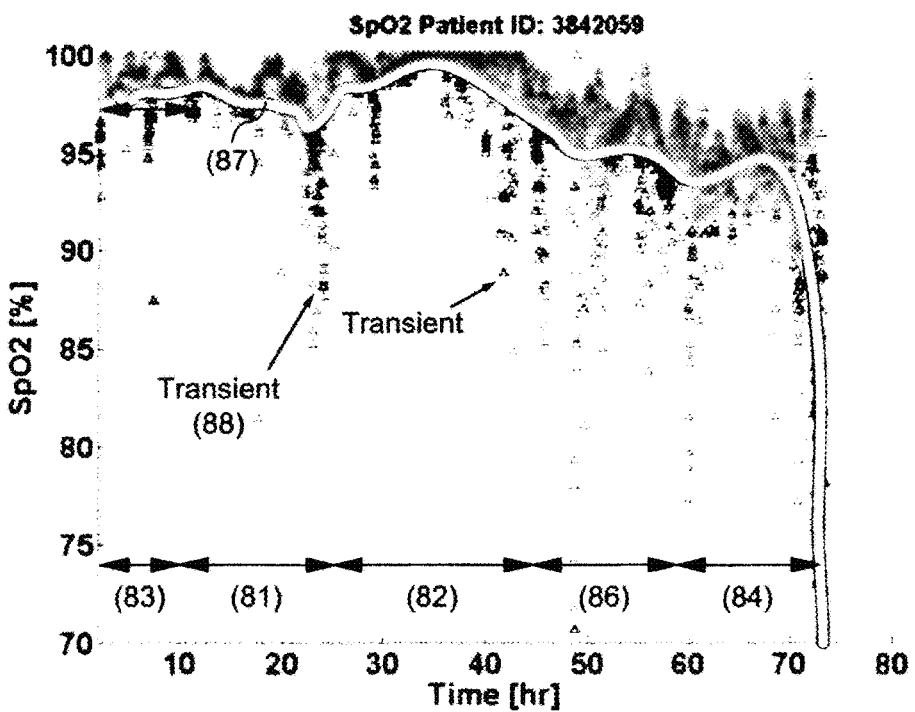
FIG. 8B depicts use of the system as it identifies transient SpO$_2$ indicators and correlates RR in FIG. 8A with the SpO$_2$ trends to prevent delayed response.

Embodiments of the system 700 can provide a service-oriented architecture or processing packages such as computing chips that process the raw data and numeric with trending analysis and pattern recognition to deliver faster, real-time notification of patient states. Where logic is incorporated into a processing chip, executable computer programs integrate the trending algorithms and pattern recognition in real-time and with security protections to protect patient data. Table 2 below shows the monitoring of $SpO_2$ over a time period of hours and the trigger that alerts a clinician automatically based on trended respiratory rate and $SpO_2$ trending. Any transient data is selected out to identify mini-trends in the overall pattern over the selected timeframe. Here, for exemplary purposes, and not limitation, a Patient #1 with an $SpO_2<90\%$ typically sets off an alarm;

with the novel pattern recognition of the invention, Patient #1 is actually in distress at 75 hours as based on correlated respiratory rate and $SpO_2$. FIG. 8 illustrates the mini-trends, selected out transient data (that which deviates outside the associated trends), and patient state (e.g. normal, unstable, stable, elevated, etc) according to those trends. FIG. 8A depicts a patient's RR recorded; a patient's $SpO_2$ is simultaneously recorded in FIG. 8B. Since the trends in RR and $SpO_2$ are collected simultaneously in real-time, the data is recorded simultaneously and correlated. The corresponding segmented trends are compared and analyzed continuously to recognize a pattern that provides an early alert as to patient distress.

TABLE 2

At least 10 hours early indication with simple anomaly detection (See FIG. 8).

| Patient | Current Monitoring - $SpO_2$ <90% violation occurs at T (hours) | Trigger on trended Resp. & $SpO_2$ occurs at T (hours) |
|---|---|---|
| 1 | 100 | 75 |
| 2 | 65 | 25 |
| 3 | 100 | 67 |
| 4 | N/A | 18 |
| 5 | 180 | 97 |
| 6 | 25 | 15 |
| 7 | 70 | 42 |
| 8 | 70 | 42 |
| 9 | N/A | 25 |

FIG. 8 illustrates where a clinician manually denotes RR as "Unstable" (81, 86), "Stable/Elevated" (82, 84), or "Normal" (83) to characterize recognized trends that can be identified as a pattern to indicate patient distress. Too many alarms are triggered when the RR trends appear to drop significantly where noisy variation (89) plays a part. FIG. 8B depicts $SpO_2$ trending data (87) with various transient data points (88) that cause at least about 90% persistent violation such that the patient has already deteriorated in condition and it is too late to act. The $SpO_2$ data and trends denoted in FIG. 8B correspond to the simultaneous collection of RR data from the patient of FIG. 8A.

CONCLUSIONS

Overall, embodiments of outlined novel schemes for early detection of respiratory distress have been disclosed. While two varied approaches to respiratory distress detection have been detailed, a synergy between the two allows amalgamation of the two techniques into a singular approach. In one embodiment, the algorithm is refined to improve the false alarm performance as well as to test the algorithm on a more extensive dataset. Furthermore, additional multi-parametric trends are identified, measured, and utilized in the analytics to expand the scope to include fields outside of respiratory distress including early detection of cardiopulmonary arrest, respiratory failure, renal failure, sepsis, and re-intubation risk, among others. To prevent silencing of critical events, the corresponding time series is processed to detect its quality and relevance within context. Descriptors as disclosed include respiratory rate, patient history, $SpO_2$, and vital signs that could also integrate patterning algorithms such as heart rate, electronic sensor monitoring, among others. Overall, non-actionable alarms are reduced to improve the confidence in sensors and machines.

Figure 9:
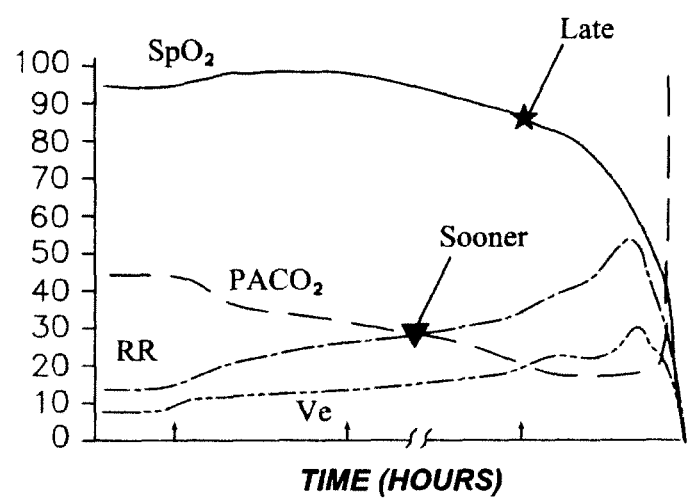
FIG. 9 demonstrates the early indication of distress in one embodiment where PACO$_2$ and RR intersect.

For exemplary purposes only, and not limitation, an embodiment of the system in FIG. 9 illustrates earlier triggering of alarms when patterns are recognized sooner rather than later. This earlier recognition improves clinician response and addresses the inaccuracy of alarm systems. The automatic recognition of trending and patterns in real-time further provides clinical systems with the monitoring and analytical capabilities that prevent false alarm fatigue and alert providers earlier as to deteriorating patient condition. As utilized herein, the system disclosed utilizes a trending algorithm to predict patient stress, particularly respiratory distress, early on. The sooner response (marked by a triangle in FIG. 9) provides early detection and warning by acknowledging simultaneous trending patterns in RR and $SpO_2$; thus, saving a patient from a detrimental occurrence when the late alarm is too late (indicated by a star in FIG. 9) in providing an urgent care response.

Without limitation, patterns of distress using an algorithm of the invention, trending and pattern recognition may utilize data from platelet count, sensor bands, neutrophil count, lymphocyte count, inflammatory markers, temperature, EKG rhythm, pulse rate, pulse variability, pulse upstroke, blood pressure, hemoglobin, $SpO_2$, respiratory rate, ventilation-oximetry, serum potassium, serum bicarbonate, serum sodium, anion gap, serum chloride, urine RBC, serum creatinine, urine WBC, urine output, among other patient data that remain misunderstood in the numbers of unexpected hospital deaths.

Embodiments taught herein may be used in a variety of applications and to monitor a variety of vital signs, and prevent false alarms in critical care, anesthesia, hemodyalysis, and others. Such information may be useful in many different types of settings throughout the hospital, within outpatient, ambulatory, or inpatient settings. Other systems may monitor vital signs from an at-home setting to recognize patterns in vital signs prior to an episode. Similar alarms algorithms can be utilized in hemodynamics analysis, cardiac, and anesthesia as mentioned above.

Having thus described several exemplary embodiments of the invention, it is to be appreciated various alterations, modifications, and improvements will readily occur to those skilled in the art. For example, in some embodiments, such alterations, modifications, and improvements are intended to be part of this disclosure, and are intended to be within the scope of the invention. Accordingly, the foregoing description and drawings are by way of example only.

What is claimed is:

1. A computer-implemented method of detecting respiratory distress in a patient, the computer including a processor, said method comprising acts of:
   learning, by the processor, a first pattern including a trending classification of respiratory rate and SpO2 using patient history data;
   monitoring, by the processor, patient data over a time period, the patient data comprising measures of respiratory rate and SpO2 recorded simultaneously in a storage component;
   tracking, by the processor, the measures of respiratory rate and SpO2 over said time period, individually, in corresponding least squares regression models, wherein tracking comprises collecting and storing the measures of respiratory rate and SpO2 in the storage component;
   analyzing, by the processor, the least squares regression models of each of the measures of respiratory rate and SpO2 to identify multiple segmented trends in each of the least squares regression models;
   removing, by the processor, a noisy deviation from the measures of respiratory rate and SpO2 by using the multiple segmented trends;

identifying, by the processor, the multiple segmented trends in each of the least squares regression models as one of an uptrend, downtrend, or neutral;

determining, by the processor, a second pattern based on the multiple segmented trends from the measures of respiratory rate and the multiple segmented trends from the measures of SpO2;

predicting, by the processor, a potential patient distress by correlating the first pattern to the second pattern; and triggering, by the processor, an alarm based on the correlation of the first pattern and the second pattern, wherein the alarm is a warning system of patient distress and prevents non-actionable alarms.

2. The computer-implemented method of claim 1, further comprising a step of correlating said measures of respiratory rate and SpO2.

3. The computer-implemented method of claim 2, wherein the first pattern is one of three types comprising:
(a) Type I: gradual decrease in SpO2 with compensatory hyperventilation;
(b) Type II: progressive minute decreases in minute ventilation and $SpO_2$; or
(c) Type III: Guarded rapid airflow including $SpO_2$ reductions followed by precipitous $SpO_2$ fall.

4. The computer-implemented method of claim 1, wherein the first pattern is learned and unique to said patient.

5. The computer-implemented method of claim 1, wherein said early warning system of patient distress indicates early detection of at least one of cardiopulmonary arrest, respiratory failure, renal failure, sepsis, and re-intubation risk.

6. The computer-implemented method of claim 1, wherein said patient data comprises measures of a plurality of vital signs, in combination.

7. The computer-implemented method of claim 6, wherein said step of tracking includes said measures of said plurality of vital signs.

8. The computer-implemented method of claim 1, wherein the first pattern comprises one of: (a) hyperventilation compensated respiratory di stress, (b) progressive unidirectional hypoventilation, or (c) sentinel rapid airflow with SpO2 reductions.

9. The computer-implemented method of claim 1, wherein said measures of respiratory rate and SpO2, individually, do not trigger an alarm, and wherein changes in said measures of respiratory rate and SpO2, in combination, trigger an alarm.

10. The computer-implemented method of claim 1, wherein said multiple segmented trends are estimated to predict patterns of progressing patient instability.

11. The computer-implemented method of claim 1, wherein said multiple segmented trends are represented by a 3-tuple time series T: {TY, t, s} wherein TY denotes each segmented trend as uptrend, downtrend, or neutral; wherein t is the time duration for which the trend component is active; and wherein s denotes the strength as a magnitude of mild, moderate, or severe such that the trend is characterized as a label vector $T_{RR/SpO2} = [T_1, T_2, T_3 \ldots T_n]$.

12. The computer-implemented method of claim 11, wherein the label vector is continuously generated and is continuously updated.

13. A computerized system for early detection of respiratory distress comprising:

one or more sensors attached to a patient to monitor a plurality of vital signs;

a monitoring system connected to said one or more sensors;

a storage component connected to said monitoring system to record patient data, wherein patient data comprises measures of the plurality of vital signs including respiratory rate and $SpO_2$ of the patient; and a processor interconnected with said monitoring system and said storage component, wherein said processor is configured to:

learn a first pattern including a trending classification of respiratory rate and $SpO_2$ using patient history data;

analyze the patient data over a time period;

analyze least squares regression models of each of the measures of respiratory rate and $SpO_2$ to identify segmented trends in the measures of respiratory rate and SpO2 simultaneously;

remove a noisy deviation from the measures of respiratory rate and $SpO_2$ by using the segmented trends;

determine a second pattern based on the segmented trends in the measures of respiratory rate and $SpO_2$;

predict a potential patient distress by correlating the first pattern to the second pattern; and trigger an alarm based on the correlation of the first pattern and the second pattern, wherein the alarm is a warning system of patient distress and prevents non-actionable alarms.

14. The computerized system of claim 13, wherein said segmented trends are identified as one of an uptrend, downtrend, or neutral using a least squares regression model.

15. The computerized system of claim 13, wherein each of said segmented trends in sequential combination establish said second pattern as the patient data is being recorded.

16. The computerized system of claim 13, wherein said measures of respiratory rate and SpO2 are recorded and correlated simultaneously.

17. The computerized system of claim 13, wherein said plurality of vital signs further comprise body temperature, pulse or heart rate, blood pressure, blood glucose, urine production, urinary incontinence, and end-tidal $CO_2$, which are correlated with said respiratory rate and SpO2, alone or in combination, to characterize said second pattern that alerts a clinician as to patient distress.

18. The computerized system of claim 13, further comprising patient history data integrated with said storage component to characterize said first pattern.

19. The computer-implemented system of claim 13, wherein said second pattern integrates patient use of any medications, sedatives, analgesics, vitamins, and supplements.

20. The computer-implemented system of claim 13, wherein the processor is a computing chip connected wirelessly to a secure network.

21. The computer-implemented system of claim 20, wherein a plurality of web-based personal devices can access said patient data and said patient status.

* * * * *